United States Patent
Nagao

(10) Patent No.: US 10,575,734 B2
(45) Date of Patent: Mar. 3, 2020

(54) PHOTOACOUSTIC INFORMATION ACQUISITION APPARATUS WITH SCAN COMPLETION TIMER BASED ON SCANNING VELOCITY

(71) Applicant: CANON KABUSHIKI KAISHA, Tokyo (JP)

(72) Inventor: Daisuke Nagao, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 439 days.

(21) Appl. No.: 14/355,099

(22) PCT Filed: Oct. 23, 2012

(86) PCT No.: PCT/JP2012/006777
§ 371 (c)(1),
(2) Date: Apr. 29, 2014

(87) PCT Pub. No.: WO2013/065249
PCT Pub. Date: May 10, 2013

(65) Prior Publication Data
US 2014/0316240 A1    Oct. 23, 2014

(30) Foreign Application Priority Data
Oct. 31, 2011    (JP) .................................. 2011-239023

(51) Int. Cl.
| | | |
|---|---|---|
| *A61B 5/00* | (2006.01) | |
| *A61B 8/00* | (2006.01) | |
| *A61B 8/08* | (2006.01) | |

(52) U.S. Cl.
CPC .......... *A61B 5/0095* (2013.01); *A61B 5/4312* (2013.01); *A61B 8/463* (2013.01);
(Continued)

(58) Field of Classification Search
CPC ........... G01R 33/5601; G01R 33/5635; A61B 5/055; A61B 5/0095; A61B 5/4312;
(Continued)

(56) References Cited

U.S. PATENT DOCUMENTS

2004/0133107 A1* 7/2004 Hashimoto ......... G01S 7/52098
600/437
2009/0187099 A1* 7/2009 Burcher ............... A61B 5/0059
600/430
(Continued)

FOREIGN PATENT DOCUMENTS

| JP | 4353975 A | 12/1992 |
|---|---|---|
| JP | 2001178717 A | 7/2001 |

(Continued)

OTHER PUBLICATIONS

Manohar et al_2004_Photoacoustic mammography laboratory prototype imaging of breast tissue phantoms, Journal of Biomedical Optics 9(6), 1172-1181, Nov./Dec. 2004.*
(Continued)

*Primary Examiner* — Serkan Akar
(74) *Attorney, Agent, or Firm* — Canon U.S.A., Inc., IP Division

(57) ABSTRACT

The present invention relates to a subject-information acquisition apparatus that receives elastic waves propagating in a subject and that acquires characteristic information of the subject, the apparatus comprising a receiver including an element that receives the elastic waves and converts the elastic waves to an electrical signal; a region designating unit that designates a region of the subject in which the characteristics information is to be acquired; a scanning unit that scans the subject with the receiver on the basis of the region; a presenting unit; and a control unit that acquires information about the time that the receiver scans the region or information about the sum of the region scanning time
(Continued)

and an additional time and that causes the presenting unit to present the acquired time information.

21 Claims, 6 Drawing Sheets

(52) U.S. Cl.
CPC .............. *A61B 8/469* (2013.01); *A61B 5/708* (2013.01); *A61B 8/0825* (2013.01); *A61B 8/42* (2013.01)

(58) Field of Classification Search
CPC ......... A61B 8/469; A61B 8/463; A61B 5/708; A61B 8/0825; A61B 8/42
See application file for complete search history.

(56) References Cited

U.S. PATENT DOCUMENTS

| | | | |
|---|---|---|---|
| 2010/0191109 A1* | 7/2010 | Fukutani | A61B 5/0059 600/437 |
| 2011/0054292 A1* | 3/2011 | Hirson | A61B 5/0073 600/407 |

FOREIGN PATENT DOCUMENTS

| | | |
|---|---|---|
| JP | 2005218520 A | 8/2005 |
| WO | 2011074656 A1 | 6/2011 |

OTHER PUBLICATIONS

Kolkman_2006_In vivo photoacoustic imaging of blood vessels with a pulsed laser diode.*

* cited by examiner

[Fig. 1]
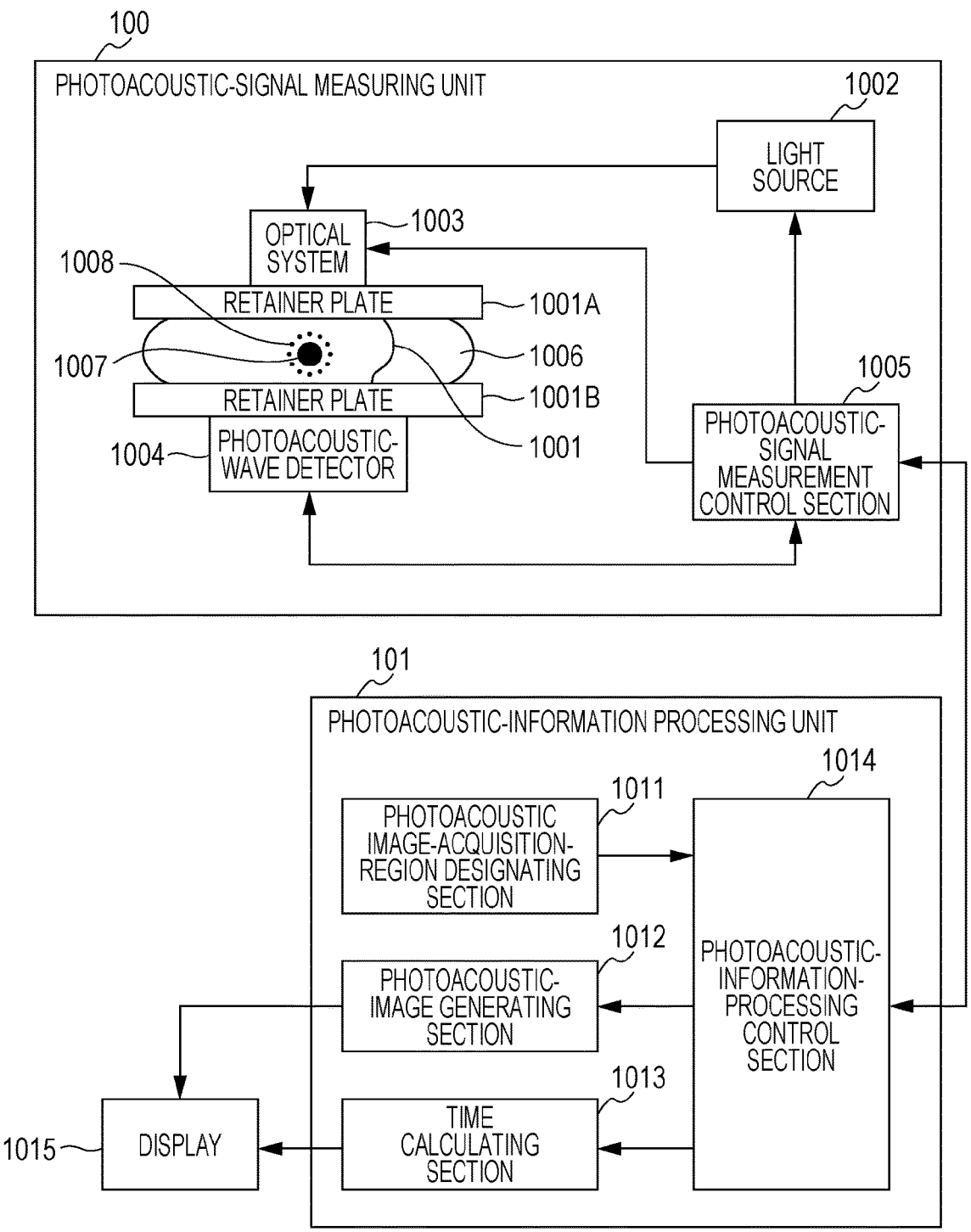

[Fig. 2]
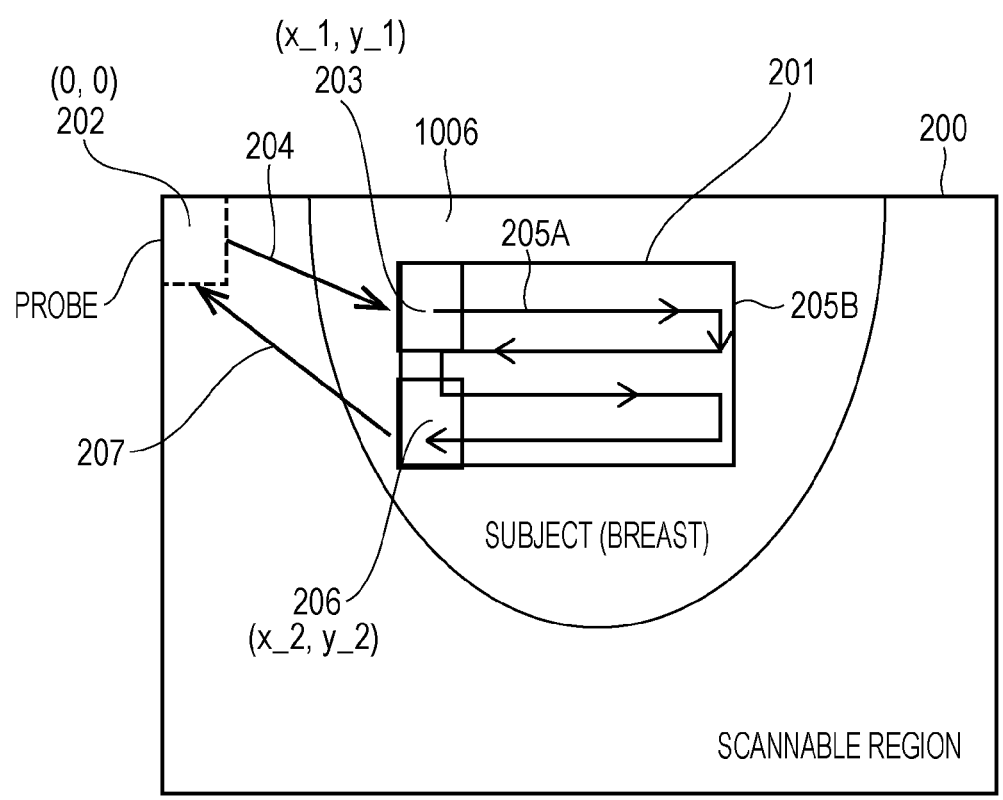

[Fig. 3]
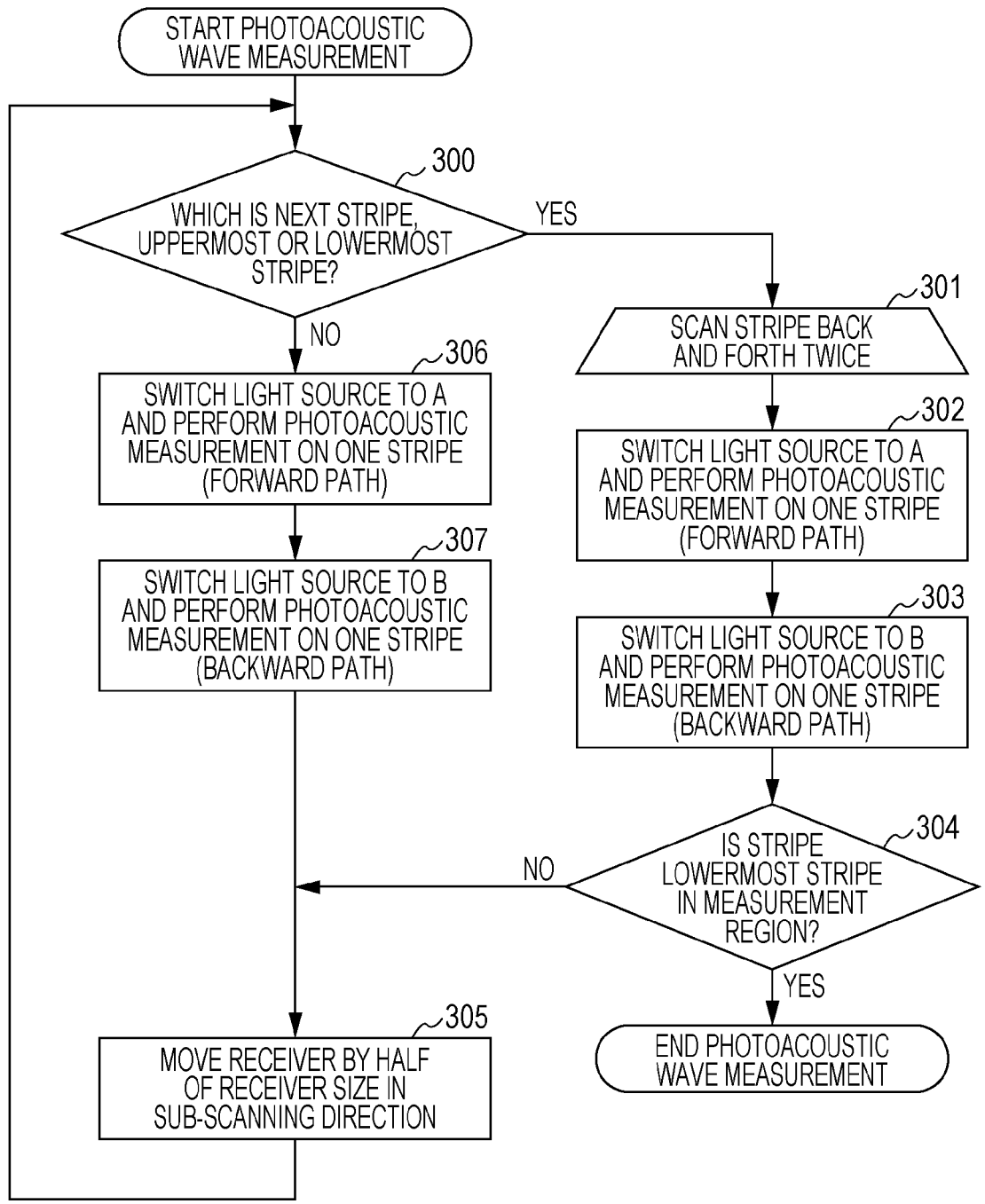

[Fig. 4]
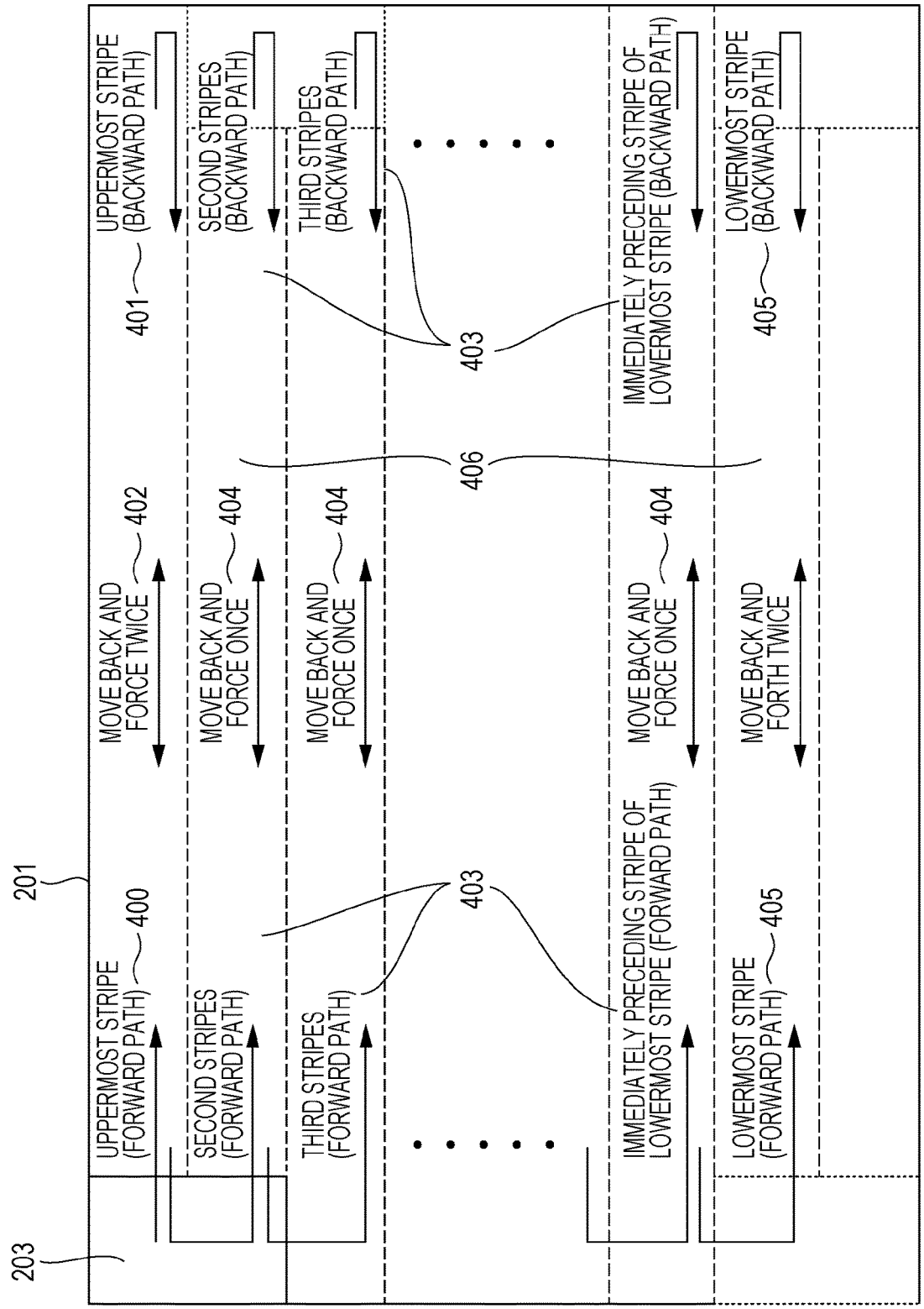

[Fig. 5]
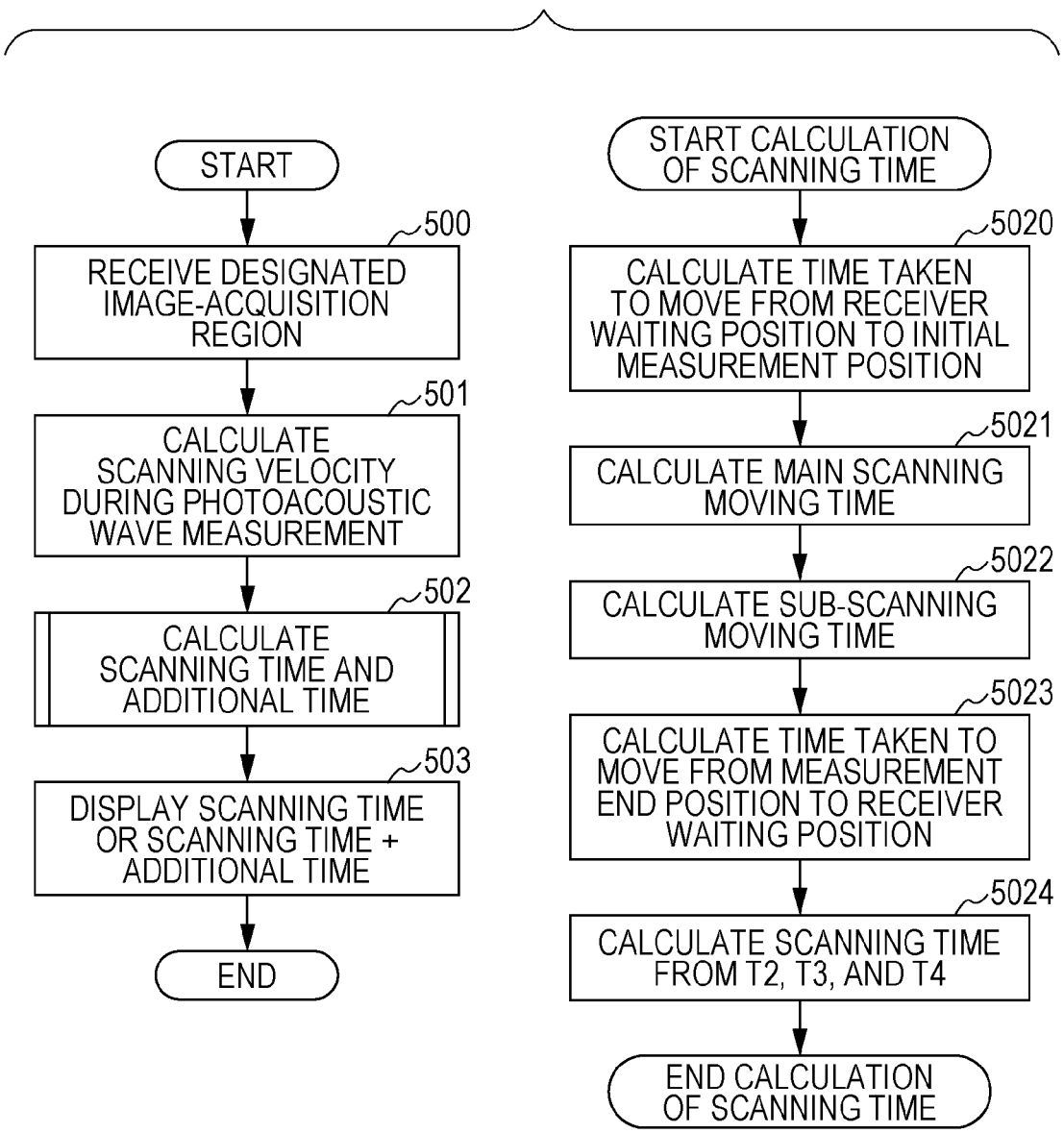

[Fig. 6]
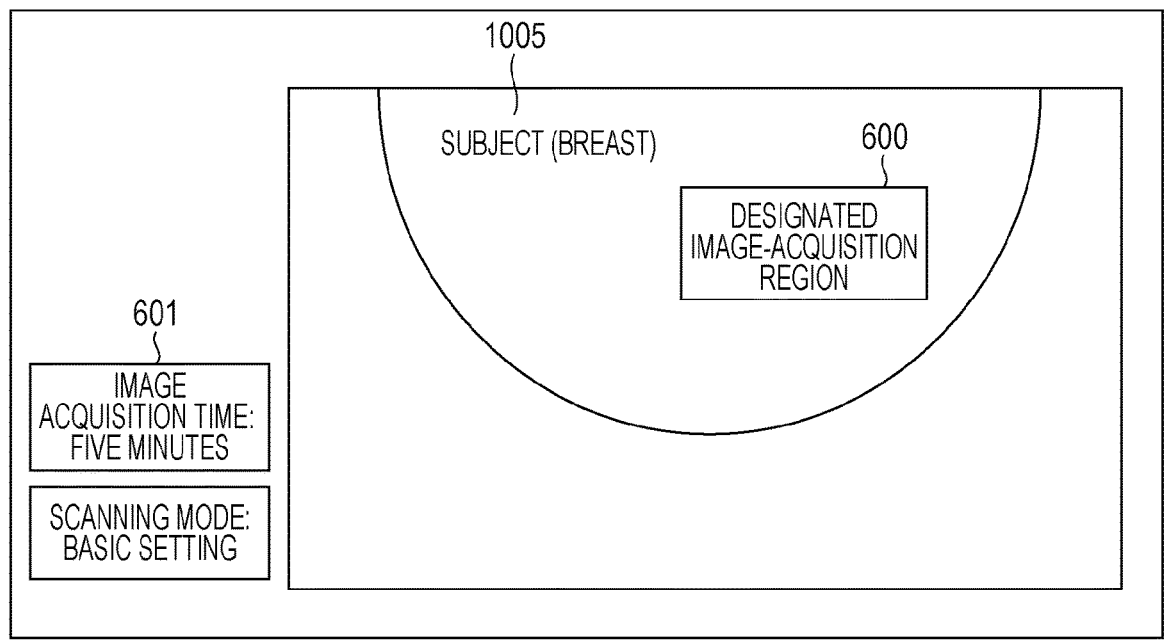

PHOTOACOUSTIC INFORMATION ACQUISITION APPARATUS WITH SCAN COMPLETION TIMER BASED ON SCANNING VELOCITY

TECHNICAL FIELD

The present invention relates to a subject-information acquisition apparatus, a method for controlling the apparatus, and a program for causing a computer to implement the control method.

BACKGROUND ART

An ultrasonic diagnostic scanner is known as diagnostic equipment for skin cancer and breast cancer. Some ultrasonic diagnostic scanners receive ultrasonic echo in a scanned region by scanning a subject with an ultrasonic-wave receiving element and acquires characteristic information (an image) of the subject in the scanned region. This technique is disclosed in PTL 1 in which a user designates an image-acquisition region of the subject in advance and acquires an image of the designated specific region. PTL 1 also describes displaying the positional relationship between the designated image-acquisition region and a maximum region in which image acquisition is allowed on a display in consideration of the size of the ultrasonic-wave receiving element.

CITATION LIST

Patent Literature

PTL 1: Japanese Patent Laid-Open No. 2005-218520

SUMMARY OF INVENTION

Technical Problem

However, the technique disclosed in PTL 1 has a problem in that the time required for image acquisition cannot be ascertained because there are no means for calculating the time taken to acquire ultrasonic echo in image acquisition and no means for calculating subject restraining time.

On the other hand, in diagnoses of skin cancer and breast cancer, diagnostic equipment using photoacoustic waves (photoacoustic tomography, hereinafter also referred to as a photoacoustic image-acquisition apparatus) has begun to be proposed in addition to the ultrasonic diagnostic scanner. The diagnostic equipment using photoacoustic waves visualizes information of biological tissue by measuring photoacoustic waves generated due to instantaneous expansion of a light absorbing substance in a living organism that has absorbed the energy of measuring light, such as visual light and near infrared rays, that irradiates the biological tissue. This photoacoustic image-acquisition technique enables a light-energy absorption density distribution, that is, the density distribution of a light absorbing substance in a living organism, to be measured quantitatively and three-dimensionally. The photoacoustic image-acquisition apparatus has a great advantage in terms of a burden on the patient because the use of light in diagnostic image acquisition enables an image-based diagnosis without exposure and invasion, and hence it is expected to be applied to breast screening and an early diagnosis, instead of X-ray apparatuses.

However, also the photoacoustic image-acquisition apparatus is required to enable the time taken for image acquisition to be ascertained, as is the foregoing ultrasonic diagnostic scanner, because it sometimes acquires (image-captures) subject information in the scanned region by scanning an element that receives photoacoustic waves over the subject.

The present invention is made in consideration of the above problem. Accordingly, the present invention provides a subject-information acquisition apparatus that acquires elastic waves, such as acoustic waves, by operating an ultrasonic probe or the like, in which information about an elastic-wave acquisition time or a subject restraining time is presented depending on an image-acquisition region designated by the user.

Solution to Problem

The present invention provides a subject-information acquisition apparatus that receives elastic waves propagating in a subject and that acquires characteristic information of the subject, the apparatus comprising a receiver including an element that receives the elastic waves and converts the elastic waves to an electrical signal; a region designating unit that designates a region of the subject in which the characteristics information is to be acquired; a scanning unit that scans the subject with the receiver on the basis of the region; a presenting unit; and a control unit that acquires information about the time that the receiver scans the region or information about the sum of the region scanning time and an additional time and that causes the presenting unit to present the acquired time information.

Advantageous Effects of Invention

According to an aspect of the present invention, since the time for acquisition of subject information (image acquisition) can be presented when subject information, the convenience for the user or the subject is enhanced.

BRIEF DESCRIPTION OF DRAWINGS

FIG. 1 is a diagram showing the configuration of a photoacoustic image-acquisition apparatus.

FIG. 2 is a diagram showing the scanning locus of a probe when an image-acquisition region is designated.

FIG. 3 is a flowchart for photoacoustic measurement of the designated image-acquisition region.

FIG. 4 is a diagram showing the scanning locus of the probe in the designated image-acquisition region.

FIG. 5 is a flowchart for calculating an image-acquisition time.

FIG. 6 is a diagram of an example of a designated image-acquisition region setting screen.

DESCRIPTION OF EMBODIMENT

An embodiment of the present invention will be described with reference to the drawings. Although this embodiment is described using a photoacoustic diagnostic (image-acquisition) apparatus as an example of the subject-information acquisition apparatus, the present invention is not limited thereto; the present invention can also be applied to an ultrasonic diagnostic scanner. The scope of the present invention is not limited to the illustrated example also in the photoacoustic diagnostic apparatus.

FIG. 1 shows, in outline, the configuration of a subject-information acquisition apparatus of this embodiment and a subject-information acquisition system including the subject-information acquisition apparatus and a presenting unit. As shown in FIG. 1, a photoacoustic image-acquisition apparatus, which is the subject-information acquisition apparatus of this embodiment, includes an acoustic-signal measuring unit 100 including at least a photoacoustic-wave detector 1004 serving as a receiver including an element that receives acoustic waves, which are elastic waves, propagating in the subject and that converts the acoustic waves to an electrical signal and a photoacoustic-signal measurement control section 1005 that is a scanning unit that causes the photoacoustic-wave detector 1004 to scan the subject on the basis of a region designated by a photoacoustic-image-acquisition-region designating section 1011 serving as a region designating unit, to be described later.

The photoacoustic image-acquisition apparatus further includes a photoacoustic-information processing unit 101 including at least the photoacoustic-image-acquisition-region designating section 1011 that designates a region in which characteristic information of the subject is to be acquired and a photoacoustic-in-formation-processing control section 1014 constituting a control unit that acquires in-formation about the time that the photoacoustic-wave detector 1004 scans the designated region or the sum of the scanning time and an additional time and that causes a display 1015 serving as a presenting unit to present the information about the acquired time.

The thus-configured subject-information acquisition apparatus of this embodiment can present information about the scanning time although the user designates an image-acquisition region, and the photoacoustic-wave detector 1004 scans the designated region to acquire characteristic information of the subject, thus providing enhanced convenience for the user or the subject. In other words, since even a subject-information acquisition apparatus in which image-acquisition time changes depending on the size and position of a designated image-acquisition region can present an image-acquisition time, the convenience for the user or the subject is enhanced.

In the subject-information acquisition apparatus of this embodiment, as shown in FIG. 1, the photoacoustic-signal measuring unit 100 further includes retainer plates 1001, a light source 1002, and an optical system 1003, and the photoacoustic-information processing unit 101 further includes a photoacoustic-image generating section 1012, and a time calculating section 1013 that constitutes the control unit together with the photoacoustic-information-processing control section 1014 described above. The subject-information acquisition system further includes the display 1015 serving as the presenting unit. The details of the photoacoustic-signal measuring unit 100, the photoacoustic-information processing unit 101, and the display 1015 will be described hereinbelow. First, the configuration of the photoacoustic-signal measuring unit 100 will be described.

In FIG. 1, the subject 1006, which is an image acquisition target, is fixed to the retainer plates 1001 that press it from both sides. The retainer plates 1001 serving as retainers are composed of a pair of retainer plates 1001A and 1001B, whose retaining positions are controlled by a retaining mechanism (not shown) to change the retaining space and pressure. If there is no need to distinguish the retainer plates 1001A and 1001B, they are collectively expressed as retainer plates 1001. The retainer plates 1001 fix the subject 1006 to the apparatus by holding it therebetween, thereby reducing measurement errors due to movement of the subject 1006. The retainer plates 1001 can adjust the thickness of the subject 1006 to a thickness suitable for photoacoustic measurement in accordance with the depth of incoming measuring light. Since the retainer plates 1001 are located on the optical path of the measuring light, they may be made of a material having high transmittance to the measuring light and high acoustic matching performance to the ultrasonic probe serving as a measuring section in the photoacoustic-wave detector 1004. For example, the retainer plates 1001 are made of polymethylpentene used in an ultrasonic diagnostic scanner and so on.

The light source 1002 radiates light to the subject 1006 to cause the subject 1006 to generate elastic acoustic waves. The light source 1002 includes two light sources (not shown, hereinafter referred to as a light source A and a light source B). The light source 1002 used is generally a solid-state laser capable of emitting pulsed light having its central wavelength in a near infrared region (for example, an yttrium-aluminum-garnet laser and a titanium-sapphire laser). The wavelength of the measuring light (light that irradiates the subject) is selected from 530 nm to 1300 nm depending on a light absorbing substance (for example, hemoglobin, glucose, and cholesterol) in the target subject 1006. For example, hemoglobin in target blood vessels that have newly grown in breast cancer generally absorbs light having wavelengths from 600 nm to 1000 nm, and a light absorber in the water constituting the living organism is the minimum in the vicinity of a wavelength of 830 nm, and thus, the optical absorption is relatively high at wavelengths from 750 nm to 850 nm. Since light absorption changes depending on the state of hemoglobin (the degree of oxygen saturation), there is a possibility that the functional changes of the living organism can be measured by comparing the changes. Although this embodiment is described using an example in which two light sources are used, one or three or more light sources may be used. The radiation frequency of the light source is normally predetermined. The radiation frequency is determined as a design value to continuously radiate pulsed light with a desired intensity. The radiation frequency may be set as high as possible because it influences the number of photoacoustic measurement per unit time. In this example, the radiation frequencies of both of the light source A and the light source B are set to 20 Hz.

The optical system 1003 for irradiating the subject 1006 in a desired shape with the measuring light coming from the light source 1002 is constituted by an optical system including a lens, a mirror, and an optical fiber and a scanning mechanism that scans over the retainer plates 1001. The optical system may be any optical system that irradiates the subject 1006 in a desired shape with the measuring light emitted from the light source 1002.

When the measuring light generated from the light source 1002 irradiates the subject 1006 via the optical system 1003, a light absorber 1007 in the subject 1006 absorbs the light and generates acoustic photoacoustic waves 1008. In this case, the light absorber 1007 corresponds to a sound source.

The photoacoustic-wave detector 1004, which is a photodetector having an element that receives the photoacoustic waves 1008 and converts them to an electrical signal, detects the photoacoustic waves 1008 and converts them to an electrical signal. The photoacoustic waves 1008 generated from the living organism are ultrasonic waves with a frequency from 100 KHz to 100 MHz. Therefore, the photoacoustic-wave detector 1004 used is an element (receiving element) that can receive the foregoing frequency band. The element (receiving element) may be any element that can detect photoacoustic waves, such as a transducer using a piezoelectric phenomenon, a transducer using optical resonance, and a transducer using a change in capacitance. The photoacoustic-wave detector 1004 of this embodiment has a plurality of receiving elements arrayed in two dimensions. The use of such two-dimensional-array elements allows the photoacoustic waves 1008 to be detected at a plurality of locations at the same time, thus reducing the detection time and reducing influences of the vibration and so on of the subject 1006. An example of the receiver has 20 receiving elements in the main scanning direction and 20 elements in the sub-scanning direction at a pitch of 4 mm. The details of the main scanning direction and the sub-scanning direction will be described later. In this embodiment, the subject 1006 is irradiated with the measuring light from the front face of the photoacoustic-wave detector 1004 serving as the receiver. Therefore, the optical system 1003 and the photoacoustic-wave detector 1004 are opposed to each other, and similar scanning control is performed at the same time so that the positional relationship therebetween is maintained.

The photoacoustic-signal measurement control section 1005 performs amplification of the electrical signal based on the photoacoustic waves obtained by the photoacoustic-wave detector 1004, analog-to-digital signal conversion, and integration for reducing noise. Furthermore, the photoacoustic-signal measurement control section 1005 transmits the photoacoustic wave signal to an external device, such as the photoacoustic-information-processing control section 1014, via an interface (not shown).

Furthermore, the photoacoustic-signal measurement control section 1005 includes a scanning unit and controls scanning of the optical system 1003 and the photoacoustic-wave detector 1004 over the subject 1006. The photoacoustic-signal measurement control section 1005 also controls driving of the light source 1002, the optical system 1003, and the photoacoustic-wave detector 1004. Description thereof will be given as follows.

The integration is performed to reduce system noise by repeating measurement at the same position of the subject 1006 and averaging the measurements, thereby improving the S/N ratio of the photoacoustic wave signal. The control of scanning of the optical system 1003 and the photoacoustic-wave detector 1004 includes scanning the optical system 1003 and the photoacoustic-wave detector 1004 over the subject 1006 in two dimensions and performs measurement at the individual scanned positions, the details of which will be described later. The scanning is performed by the photoacoustic-signal measurement control section 1005 including the scanning unit on the basis of a region (region in which subject characteristic information is to be obtained) designated by the photoacoustic-image-acquisition-region designating section 1011, to be described later. By scanning the photoacoustic-wave detector 1004 over the subject 1006 in this way, necessary acoustic waves can be obtained in a wide image-acquisition region even with a small probe. For example, for breast imaging, a photoacoustic image of full breast can be acquired. The image-acquisition region is a region in which three-dimensional volume data calculated on the basis of the measured photoacoustic waves is to be acquired. Examples of the control of the light source 1002 include selection between the light source A and the light source B and determination of laser emission timing. Examples of the control of the optical system 1003 and the photoacoustic-wave detector 1004 include movement control (moving to an appropriate position) related to the additional time, to be described later.

Next, the photoacoustic-information processing unit 101 will be described.

The photoacoustic-information processing unit 101 generates and displays a photoacoustic image on the basis of photoacoustic-wave measurement data received from the photoacoustic-signal measuring unit 100, designates a region in which subject characteristic information is to be acquired (also referred to as an image-acquisition region), calculates and acquires the time for subject restraint on the basis of the designated image-acquisition region, and displays the information about the acquired time. The photoacoustic-information processing unit 101 used generally has a high-performance processing function and graphic display function, such as a personal computer and a workstation.

The photoacoustic-image-acquisition-region designating section 1011 that designates a region in which subject characteristic information is to be acquired has means for the user to designate an image-acquisition region. The user designates the image-acquisition region with an input unit, such as a mouse. The input unit is not limited to a mouse or a keyboard but may be a pen tablet or a touch pad attached to the surface of the display. Designation of the image-acquisition region can be made on the basis of an image acquired by a camera (not shown) disposed in a direction perpendicular to the retainer plates 1001 that retain the subject 1006 with pressure.

The photoacoustic-information-processing control section 1014 that constitutes the control unit receives information of the region in which the subject characteristic information is to be acquired, which is acquired by the photoacoustic-image-acquisition-region designating section 1011, calculates information about the scanning time or the sum of the scanning time and the additional time, to be described later, together with the time calculating section 1013, to be described later, and displays the time information on the display 1015 serving as the presenting unit. The time calculating section 1013, which constitutes the control unit together with the photoacoustic-information-processing control section 1014, calculates the time required to acquire elastic acoustic waves, the time that the photoacoustic-wave detector 1004 scans the subject 1006, and the time for restraining the subject 1006, details of which will be described later. The time for restraining the subject 1006 includes the foregoing scanning time and the additional time described later.

The time taken to acquire acoustic waves calculated by the time calculating section 1013 or the subject restraining time is displayed on the display 1015 in accordance with an instruction from the time calculating section 1013 that constitutes the control unit together with the photoacoustic-information-processing control section 1014.

By acquiring subject characteristic information with the thus-configured photoacoustic image-acquisition apparatus on the basis of the photoacoustic effect, the optical characteristic distribution of the subject 1006 can be imaged, and the photoacoustic image can be presented.

In FIG. 1, although the photoacoustic-signal measuring unit 100 and the photoacoustic-information processing unit 101 are separate hardware, the functions thereof may be integrated to one.

Next, a method for controlling the photoacoustic image-acquisition apparatus serving as the subject-information acquisition apparatus will be described on the basis of the configuration of the photoacoustic image-acquisition apparatus described above.

The method for controlling the photoacoustic image-acquisition apparatus of this embodiment has the following steps:

receiving information about a region of the subject, designated by a user, in which the characteristics information is to be acquired; scanning the subject with a receiver including an element that receives the elastic waves and converts the elastic waves to an electrical signal on the basis of the designated region; acquiring information about the time that the receiver scans the region or information about the sum of the region scanning time and an additional time; and presenting the acquired time information on a presenting unit.

The individual steps will be described hereinbelow in detail.

(Step of receiving information about a region of the subject, designated by a user, in which the characteristics information is to be acquired)

Designation of the image-acquisition region can be made by the user by using the input unit, such as a mouse, described above, on the basis of an image acquired by a camera (not shown) disposed in the direction perpendicular to the retainer plates 1001 that retain the subject 1006 with pressure. The user designates an image-acquisition region with the intention of acquiring three-dimensional volume data including the depth portion in the acquired image on the basis of the acquired image. The photoacoustic-information-processing control section 1014 receives the signal of the image-acquisition region.

(Step of scanning the subject with a receiver including an element that receives the elastic waves and converts the elastic waves to an electrical signal on the basis of the designated region)

The photoacoustic-wave detector 1004 is scanned in two dimensions along the retainer plates 1001 so that the three-dimensional volume data of the image-acquisition region designated by the user can be acquired. The photoacoustic-wave detector 1004 is controlled so that the coordinates of the acquired image is converted to the coordinates of the scanned region and that the photoacoustic-wave detector 1004 is moved to the corresponding position of the actual subject 1006.

Referring to FIG. 2, the details of scanning and movement of the photoacoustic-wave detector 1004 will be described.

The conceptual diagram of FIG. 2 shows the scanning locus of the center of the photoacoustic-wave detector 1004 when an image-acquisition region is designated.

A scannable region 200 is the maximum scanning region on the scan surface, and a designated scanning region 201 is a scanning region on the scan surface corresponding to the designated image-acquisition region. The photoacoustic-wave detector 1004 moves from a waiting position 202 to the initial position of the designated scanning region, 203 (see arrow 204 in FIG. 2). Subsequently, the whole of the designated scanning region 201 is scanned in the main scanning direction 205A and the sub-scanning direction 205B to perform photoacoustic measurement. Subsequently, the photoacoustic-wave detector 1004 moves from a scanning end position 206 to the waiting position 202 (see arrow 207).

Next, the details of scanning of the photoacoustic-wave detector 1004 in the designated scanning region will be described.

A flowchart in FIG. 3 shows the flow of photoacoustic measurement of the designated scanning region 201 in FIG. 2.

Here, this embodiment assumes that the number of integrations of photoacoustic wave data per pixel is set to 40 by way of example. In the example of this embodiment, since the number of elements of the probe is 20 in the main scanning direction, and the number of integrations is set to 40, 20 times of integration can be performed during one forward movement (ditto for one backward movement) by moving the probe one receiving element at a time.

Here, the region in which the probe is moved in the main scanning direction to perform photoacoustic measurement is defined as a stripe. In this embodiment, the size of the region in which a photoacoustic wave signal can be acquired due to one light emission from the light source is the size of the whole element region of the probe. Although the region in which the photoacoustic measurement is actually performed is a three-dimensional region including the depthwise direction, a plane of the region where the photoacoustic measurement is performed cut out in parallel to the scanning of the probe is referred to as a stripe, unless otherwise specified.

Referring to the flowchart in FIG. 3, the flow of the photoacoustic measurement of the designated image-acquisition region will be described.

After the image-acquisition region designated by the user is received by the photoacoustic-information-processing control section 1014, and the probe has moved to the designated-scanning-region initial position 203, photoacoustic measurement is started.

In step 300, it is determined whether the next measurement stripe is the uppermost stripe or the lowermost stripe in the designated image-acquisition region, that is, whether the first or the last stripe of the measurement.

If YES (Y) in step 300, the target stripe is scanned back and forth twice (step 301). In step 302, the light source is switched to the light source A, and photoacoustic measurement of one stripe (forward path) is performed. In step 303, the light source is switched to the light source B, and photoacoustic measurement of the one stripe (backward path) is performed. The reason why the photoacoustic-wave detector 1004 is moved back and force on the target stripe twice is that, in this example, the number of integrations is 40 for the light source A and the light source B, and the number of integrations for one stripe is 20.

Next, in step 304, it is determined whether the measurement stripe is the lowermost stripe in the measurement region. If YES (Y) in step 304, that is, it is the lowermost stripe, the photoacoustic measurement of the designated image-acquisition region ends. If NO (N) in step 304, the photoacoustic-wave detector 1004 is moved in the sub-scanning direction by half of the size thereof. The photoacoustic-wave detector 1004 is moved by half of the size thereof so that the measurement cab be performed on all the pixels of the designated image-acquisition region with the receiving elements of the photoacoustic-wave detector 1004 as much as possible.

If NO (N) in step 300, the light source is switched to the light source A, and photoacoustic measurement of one stripe (forward path) is performed (step 306). Next, the light source is switched to the light source B, and photoacoustic measurement of the one stripe (backward path) is performed (step 307). Next, the photoacoustic-wave detector 1004 is moved by half of the size of the photoacoustic-wave detector 1004 in the sub-scanning direction (step 305). Since the photoacoustic-wave detector 1004 is moved by half of the size thereof every stripe, the number of integrations for both of the light source A and the light source B reaches 40 by one back and forth movement, except for the uppermost and lowermost stripes.

Referring next to FIG. 4, the foregoing scanning locus will be conceptually described in detail. The forward path of the uppermost stripe 400 from the designated-scanning-region initial position 203 is subjected to photoacoustic measurement by using the light source A, and the backward path 401 of the uppermost stripe is subjected to photoacoustic measurement by using the light source B, which are performed twice (402). Next, the second stripe to the immediately preceding stripe of the lowermost stripe, 403, are subjected to photoacoustic measurement, in which the light source A is used for the forward path, and the light source B is used for the backward path, which are performed once (404). The lowermost stripe 405 is subjected to the same scanning as for the uppermost stripe, described above. Although the number of integrations for the lower half of the uppermost stripe, or at least the upper half of the lowermost stripe, exceeds 40, there is no problem because it leads to an increase in S/N ratio. Region 406 is the region in which the number of integrations exceeds 40.

Next, actual time calculation will be described with reference to a flowchart in FIG. 5.

(Step of acquiring information about the time that the receiver scans the region or information about the sum of the region scanning time and an additional time)

Accurate image acquisition of the photoacoustic image-acquisition apparatus requires that the subject 1006 is stand still, which needs to restrain the subject 1006 in some way, such as fixing part of the body. Particularly in image acquisition of a breast of the subject 1006, the subject 1006 is restrained, with the breast fixed under pressure. Since the restraint of the subject 1006 often causes pain, information of the time from the start of image acquisition to the release of the subject 1006 is useful for a doctor and a technician who perform image acquisition and the subject 1006. Even if no pressure is applied, the image acquisition has to be performed, with the subject 1006 at a standstill, and thus, the subject 1006 is restrained. Thus, the time from the start of image acquisition to the release of the subject 1006 is referred to as a restraining time, which is divided into a receiver scanning time and an additional time, and the following description is made.

The scanning time is the time that the receiver scans the designated image-acquisition region, and the additional time is, for example, the time that the receiver moves between the waiting position and the designated image-acquisition region. This will be specifically described with a series of operations (1) to (4) as follows:

(1) Designated-scanning-region initial-position moving time T1 during which the photoacoustic-wave detector 1004 serving as the receiver moves simply from the waiting position 202 to the designated-scanning-region initial position 203

(2) Main-scanning moving time T2 during which the photoacoustic-wave detector 1004 moves while acquiring photoacoustic waves of the designated scanning region in the main scanning direction 205A (3) Sub-scanning moving time T3 during which the photoacoustic-wave detector 1004 moves simply in the sub-scanning direction 205B of the designated scanning region (4) Receiver waiting-position moving time T4 during which the photoacoustic-wave detector 1004 moves simply from the scanning end position 206 to the waiting position 202

In (1) to (4), the scanning time is the sum of T2 and T3, and the additional time is T4 or T1+T4.

In the above operation, the time calculating section 1013 calculates the sum of T2+T3 as the scanning time on the basis of the size of the designated region and calculates T4 or T1+T4 as the additional time on the basis of the position of the designated region. This will be described below.

First, calculation of the scanning time will be described.

In step 500, the photoacoustic-information-processing control section 1014 receives the image-acquisition region that the user designates with the photoacoustic-image-acquisition-region designating section 1011. An example of the designation of the image-acquisition region is shown in FIG. 6. Reference numeral 600 denotes the image-acquisition region designated by the user. In this case, photoacoustic measurement conditions can also be set. In this embodiment, although the scanning method of repeating main scanning and sub-scanning is described by way of example, another method, such as spiral scanning, may be selected.

In step 501, the scanning velocity during photoacoustic measurement is calculated. The scanning velocity Vx (mm/sec) and the number of times of scanning, Sn (times), of the photoacoustic-wave detector 1004 and the laser light source in the main scanning direction are calculated using the following equations:

$$Vx = Epitcha * LHz \quad \text{(Eq. 1)}$$

$$Sn = (Mn/Enxa) * 2 * (\tfrac{1}{2}) \quad \text{(Eq. 2)}$$

where Enxa(elements) is the number of elements of the photoacoustic-wave detector 1004 in the main scanning direction, Epitcha (mm) is the element pitch in the main scanning direction, Mn (times) is the number of integrations of photoacoustic measurement, and LHz (Hz) is the emission frequency of the laser light source. For ease of explanation, the number of integrations, Mn, is set to be a multiple of the number of elements, Enxa.

In the example of this embodiment, since the number of elements of the probe is 20 in the main scanning direction, and the number of integrations is set to 40, as described above, 40 times of integration can be performed by moving the photoacoustic-wave detector 1004 one receiving element at a time.

Accordingly, if the element pitch of one reciprocating motion is 4 mm, and the emission frequency of the laser light source is 20 Hz, the scanning velocity during measurement is 80 mm/sec.

The foregoing calculation of the scanning velocity, that is, the calculation of the scanning velocity based on the pitch of the plurality of elements arrayed in the scanning direction and the emission frequency of the light source, is performed by a velocity calculating unit provided in the photoacoustic-information-processing control section 1014. The scanning time is calculated and acquired on the basis of the calculation result of the velocity calculating unit.

Under more complicated conditions in which the number of integrations is smaller than the number of elements in the main scanning direction, Enxa, or is a multiple of a value smaller than Enxa, the number of integrations per reciprocation of the photoacoustic-wave detector 1004 is small. In this case, since the photoacoustic-wave detector 1004 can scan two or more pixels per unit time, the scanning velocity can be set higher. The method for setting the moving velocity of the probe is not limited to the method of the example of this embodiment; various algorithms may be applied to adjust the scanning velocity, depending on the measurement conditions and apparatus configuration.

Since the scanning-velocity calculating function of this embodiment aims at obtaining the moving velocity of the photoacoustic-wave detector 1004 for photoacoustic measurement, the reference parameters and algorithms are not limited to those described in the above example.

In step 502, the scanning time and the additional time are calculated.

In step 5020, first, moving time T1 to the scanning-region initial position is calculated. The moving time T1 to the scanning-region initial position is expressed by the following equation:

[Math. 1]

$$T1 = \frac{\sqrt{X\_1^2 + Y\_1^2}}{Vxy} \quad \text{(Eq. 3)}$$

where the coordinates of the waiting position of the photoacoustic-wave detector 1004 is (0, 0), the designated-scanning-region initial position is (X_1, Y_1), and Vxy (mm/sec) is the velocity (moving velocity) of the photoacoustic-wave detector 1004 except during photoacoustic measurement.

In step 5021, main-scanning moving time T2 is calculated. Here, the number of stripes covering the designated scanning region, N, when the moving distance in the sub-scanning direction is set to half of the size of the photoacoustic-wave detector 1004 is expressed by the following equation:

[Math. 2]

$$N = ceil\left(\frac{Ys}{\frac{Enxb \times Epitchb}{2}}\right) \quad \text{(Eq. 4)}$$

where Ys is the length of the designated scanning region in the sub-scanning direction (Y-direction), Enxb is the number of elements of the photoacoustic-wave detector 1004 in the sub-scanning direction (Y-direction), Epitchb is the pixel pitch. The derived N represents the number of times that the probe moves from one end to the other end.

Accordingly, the total moving distance in the main scanning direction in the designated scanning region is expressed as Xs*(N+1)*Sn, where Xs is the length of the designated scanning region in the main scanning direction. Accordingly, the main-scanning moving time T2 is expressed by the following equation:

[Math. 3]

$$T2 = \frac{Xs \times (N+1) \times Sn}{Vx} \quad \text{(Eq. 5)}$$

where Vx is the scanning velocity in the main scanning direction, which is 80 mm/sec in the above example.

In step 5022, sub-scanning moving time T3 is calculated. The sub-scanning moving time T3 is expressed by the following equation:

[Math. 4]

$$T3 = \frac{Ys}{Vxy} \quad \text{(Eq. 6)}$$

In step 5023, waiting-position moving time T4 of the receiver (photoacoustic-wave detector 1004), which is an additional time, is calculated. If the scanning end position is (X_2, Y_2), the receiver waiting-position moving time T4 is expressed by the following equation:

[Math. 5]

$$T4 = \frac{\sqrt{X\_2^2 + Y\_2^2}}{Vxy} \quad \text{(Eq. 7)}$$

where Vxy may be set equal to Vx for simplification of the apparatus configuration.

In step 5024, scanning time T5 and additional time T6 are calculated, which are expressed by the following equations:

$$T5 = T2 + T3$$

$$T6 = T4.$$

Although the scanning velocity used in the scanning-time calculation is constant, a more rigorous scanning velocity in which the initial acceleration or the like is taken into account may be used. The scanning velocity used in the scanning-time calculation is not limited to that of this example. For example, if the subject 1006 is pressed before the start of image acquisition, the additional time may be set to T1+T4, and furthermore, the pressing mechanism (retainer plates 1001) releasing time may be included in the additional time.

In step 503, the calculated scanning time T5 or the sum of the scanning time T5 and the additional time T6 is displayed on the display 1015. It may be expressed as a character, such as a numeral, as denoted by 601 in FIG. 6, a gauge, or time. Alternatively, it may be announced by sound or the like. Not the scanning time T5 or the sum of the scanning time T5 and the additional time T6 is presented directly, but information about the scanning time T5 or the sum of the scanning time T5 and the additional time T6 may be presented. Specifically, the difference between the scanning time T5 and the time that has elapsed from the start of image acquisition, that is, the remaining time of the image acquisition, or the difference from the sum of the times T5 and T6 and the time that has elapsed from the start of image acquisition, that is, the remaining restraining time, may be presented.

Although this embodiment shows the example in which the scanning time or the sum of the scanning time and the moving time of the receiver from the waiting position to the image-acquisition region is calculated and presented, an additional time in which the total time required for the restraint of the subject 1006 or the time required for releasing the subject 1006 may be obtained, and a more accurate restraining time calculated from the additional time may be displayed.

The timing of presentation of the scanning time or the sum of the scanning time and the additional time may be in synchronization with the start of image acquisition or may be directly after time calculation. For example, the calculated time (the scanning time or the sum of the scanning time and the additional time) may be presented during the designation of the image-acquisition region by the user on the basis of the size and position thereof.

A computer program for executing the foregoing control method is also included in the scope of the present invention.

Although an embodiment of the present invention has been described, the present invention is not limited to the embodiment, and various modifications and changes can be made within the scope of the invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-239023, filed Oct. 31, 2011, which is hereby incorporated by reference herein in its entirety.

The invention claimed is:

1. A subject-information acquisition apparatus, the apparatus comprising:
a light emitting end optically connected to a light source and configured to emit light onto a subject for a plurality of times with an emission frequency to cause the subject to generate elastic waves;
a receiver including a plurality of elements arranged at an array pitch in a scanning direction and configured to receive the elastic waves from the subject and convert the elastic waves to an electrical signal;
a display unit configured to display an image of the subject;
a region designator configured to designate a region of the subject based on the displayed image and a designation from a user, wherein the designated region is a region in which characteristics information of the subject is to be acquired;
a scanner configured to scan the designated region of the subject; and
a controller including a velocity calculating unit configured to calculate a scanning velocity at which the receiver scans the subject based on the emission frequency and the array pitch, and configured to acquire time information on a remaining time for completion of scanning of the designated region based on a calculated result of the velocity calculating unit, and configured to cause the display unit to display the acquired time information.

2. The subject-information acquisition apparatus according to claim 1, wherein the time information includes the time that the receiver moves between a waiting position of the receiver and the designated region.

3. The subject-information acquisition apparatus according to claim 1,
wherein the display unit displays, as the time information, information about the time that the receiver scans the designated region or information about the sum of the designated region scanning time and an additional time in accordance with an instruction from the controller.

4. The subject-information acquisition apparatus according to claim 1, wherein the scanner is configured to mechanically move the receiver relative to the subject.

5. The subject-information acquisition apparatus according to claim 1, further comprising:
an image capturing unit that captures an external image of the subject; and
an input unit for designating a region in the external image,
wherein the region designator designates the region in which the characteristic information is to be acquired, based on a designation made via the input unit.

6. The subject-information acquisition apparatus according to claim 1, wherein the information about the remaining time is sound information or visual information.

7. The subject-information acquisition apparatus according to claim 1, wherein the scanner is configured to mechanically move the receiver relative to the subject.

8. The subject-information acquisition apparatus according to claim 1, further comprising a restraining unit configured to restrain the subject while the scanner scans the subject.

9. The subject-information acquisition apparatus according to claim 8,
wherein the acquired time information includes a time remaining for completion of movement of the receiver relative to the subject while the subject remains restrained.

10. A method for controlling a subject-information acquisition apparatus, the method comprising the steps of:
receiving information about a region of a subject, designated by a user, in which characteristics information is to be acquired;
receiving information about a scanning condition for the designated region of the subject;
irradiating a subject with a light emitting end that is optically connected to a light source and configured to emit light onto the subject for a plurality of times with an emission frequency to cause the subject to generate elastic waves;
scanning the subject with a receiver that includes a plurality of elements arranged at an array pitch in a scanning direction, receives the elastic waves, and converts the elastic waves to an electrical signal on the basis of the designated region;
calculating a scanning velocity at which the receiver scans the subject based on the emission frequency of the light source and the array pitch of the elements; and
acquiring time information including a remaining time for completion of scanning of the designated region based on the received information about the designated region of the subject and the scanning condition and a calculated result of the calculating step; and
causing a display unit to display an image of the subject along with the acquired time information.

11. The method for controlling a subject-information acquisition apparatus according to claim 10, further comprising;
restraining the subject while the scanner scans the subject with the receiver.

12. The method for controlling a subject-information acquisition apparatus according to claim 11, further comprising:
displaying the acquired time information on the display unit,
wherein the acquired time information includes a time remaining for completion of movement of the receiver relative to the subject while the subject remains restrained.

13. A subject-information acquisition apparatus, the apparatus comprising:
a light emitting end optically connected to a light source and configured to emit light onto a subject for a plurality of times with an emission frequency to cause the subject to generate elastic waves;
a receiver including a plurality of elements arranged in a scanning direction at an array pitch and configured to receive elastic waves propagated from the subject;
a region designator configured to designate a region in which characteristics information of the subject is to be acquired;
a display unit configured to display an image of the subject; and
a controller including a velocity calculating unit configured to calculate a scanning velocity at which the receiver scans the subject based on the emission frequency and the array pitch, and configured to acquire time information about a remaining time for completion of scanning of the designated region based on a calculated result of the velocity calculating unit, and configured to cause the display unit to display information about the remaining time for completion and information about the region designated by the region designator.

14. The subject-information acquisition apparatus according to claim 13, further comprising a scanner that causes the receiver to scan the subject,
wherein the controller causes the display unit to present information about time required for the receiver to scan the designated region as the information about the remaining time.

15. The subject-information acquisition apparatus according to claim 13, further comprising a retaining member that retains the subject,
wherein the controller causes the display unit to present information about time during which the subject is to be retained by the retaining member as the information about the remaining time.

16. The subject-information acquisition apparatus according to claim 13, wherein the remaining time includes time that the receiver moves between a waiting position of the receiver and the designated region.

17. The subject-information acquisition apparatus according to claim 13, further comprising:
an image capturing unit that captures an external image of the subject; and
an input unit for designating a region in the external image,
wherein the region designator designates the region in which the characteristic information is to be acquired, based on a designation made via the input unit.

18. The subject-information acquisition apparatus according to claim 13, wherein the information about the remaining time is sound information or visual information.

19. The subject-information acquisition apparatus according to claim 13, further comprising the display unit.

20. The subject-information acquisition apparatus according to claim 13, further comprising a restraining unit configured to restrain the subject while the receiver receives elastic waves propagated from the subject.

21. The subject-information acquisition apparatus according to claim 20,
wherein the remaining time includes a time remaining for the completion of acquiring information about the designated region while the subject is restrained.

* * * * *